US00PP16374P2

(12) United States Plant Patent
Baars

(10) Patent No.: US PP16,374 P2
(45) Date of Patent: Mar. 21, 2006

(54) ***FICUS* PLANT NAMED 'BELIZE'**

(50) Latin Name: *Ficus elastica*
Varietal Denomination: Belize

(75) Inventor: Johannes Baars, Uitgeest (NL)

(73) Assignee: Oro Farms Inc., Bountiful, UT (US)

( * ) Notice: Subject to any disclaimer, the term of this patent is extended or adjusted under 35 U.S.C. 154(b) by 3 days.

(21) Appl. No.: 11/041,612

(22) Filed: Jan. 22, 2005

(51) Int. Cl.
*A01H 5/00* (2006.01)

(52) U.S. Cl. ..... Plt./211
(58) Field of Classification Search ..... Plt./211
See application file for complete search history.

(56) References Cited

PUBLICATIONS

UPOV–ROM GTITM Computer Database 2003/03, GTI Jouve Retrieval Software, Citation for 'Belize'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct *Ficus* plant named 'Belize', characterized by its upright and columnar plant form; dark greenish red-colored stems; red purple, green and white variegated leaves; and red purple-colored leaf venation and petioles.

1 Drawing Sheet

Botanical designation: *Ficus elastica.*
Cultivar Denomination: 'Belize'.

CROSS-REFERENCE TO RELATED APPLICATIONS

The present application is co-pending with the following related application: *Ficus* Plant Named 'Brasil' Plant patent application No. 11/041,805; Johannes Baars, applicant.

BACKGROUND OF THE INVENTION

The present invention relates to a new and distinct cultivar of *Ficus,* botanically known as *Ficus elastica,* and hereinafter referred to by the name 'Belize'.

The new *Ficus* is a naturally-occurring whole plant mutation of *Ficus elastica* cultivar Tineke, not patented. The new *Ficus* was discovered and selected by the Inventor in a controlled environment in Uitgeest, The Netherlands in March, 1999 within a population of plants of the cultivar Tineke. The selection of this whole plant mutation was based on its unique leaf coloration.

Asexual reproduction of the new *Ficus* by cuttings in a controlled environment in Uitgeest, The Netherlands, since June, 1999, has shown that the unique features of this new *Ficus* are stable and reproduced true to type in successive generations.

SUMMARY OF THE INVENTION

The cultivar Belize has not been observed under all possible environmental conditions. The phenotype may vary somewhat with variations in environmental and cultural practices such as temperature and light intensity without, however, any variance in genotype.

The following traits have been repeatedly observed and are determined to be the unique characteristics of 'Belize'. These characteristics in combination distinguish 'Belize' as a new and distinct cultivar of *Ficus.*

1. Upright and columnar plant form.
2. Dark greenish red-colored stems.
3. Red purple, green and white variegated leaves.
4. Red purple-colored leaf venation and petioles.

Plants of the new *Ficus* differ from plants of the parent, the cultivar Tineke, in the following characteristics:

1. Plants of the new *Ficus* and the cultivar Tineke differ in stem coloration as plants of the cultivar Tineke have light green-colored stems.
2. Plants of the new *Ficus* and the cultivar Tineke differ in leaf coloration as plants of the cultivar Tineke have green and white-colored leaves.
3. Plants of the new *Ficus* and the cultivar Tineke differ in leaf vein and petiole coloration as plants of the cultivar Tineke have light green-colored leaf veins and petioles.

Plants of the new *Ficus* can be compared to plants of the *Ficus* cultivar Brasil, disclosed in a U.S. Plant patent application Ser. No. 11/041,805. In side-by-side comparisons conducted in Uitgeest, The Netherlands, plants of the new *Ficus* and the cultivar Brasil differed in the following characteristics:

1. Plants of the new *Ficus* were taller and had longer internodes than plants of the cultivar Brasil.
2. Plants of the new *Ficus* and the cultivar Brasil differed in leaf colorations as plants of the cultivar Brasil had green, grayed green and white-colored leaves.

BRIEF DESCRIPTION OF THE PHOTOGRAPH

The accompanying colored photograph illustrates the overall appearance of the new *Ficus,* showing the colors as true as it is reasonably possible to obtain in colored reproductions of this type. Colors in the photograph may differ slightly from the color values cited in the detailed botanical description which accurately describe the colors of the new

*Ficus.* The photograph comprises a side perspective view of typical plants of 'Belize' grown in a container.

DETAILED BOTANICAL DESCRIPTION

The aforementioned photographs and following observations and measurements describe plants grown in Uitgeest, The Netherlands in a glass-covered greenhouse during the summer and autumn under conditions which closely approximate commercial production. During the production of the plants, day temperatures were about 22° C., night temperatures were about 20° C. and light levels were about 6,000 lux. Plants were about 20 weeks old when the photographs and the description were taken. In the description color references are made to The Royal Horticultural Society Colour Chart, 1995 Edition, except where general terms of ordinary dictionary significance are used.

Botanical classification: *Ficus elastica* cultivar Belize.

Parentage: Naturally-occurring whole plant mutation of *Ficus elastica* cultivar Tineke, not patented.

Propagation:

*Type.*—By cuttings.

*Time to initiate roots.*—About 8 days.

*Time to produce a rooted young plant, summer.*—About 42 days.

*Time to produce a rooted young plant, winter.*—About 48 days.

*Root description.*—Thick, fibrous, fleshy; white to light orange in color.

*Rooting habit.*—Freely branching; moderately dense.

Plant description:

*Plant form and growth habit.*—Upright and columnar plant habit. Moderately vigorous.

*Branching habit.*—Two to three lateral branches will develop if plants are pinched.

*Plant height.*—About 60 cm.

*Plant diameter* (*area of spread*).—About 23 cm.

*Stem description.*—Length: About 50 cm. Diameter: About 2 cm. Internode length: About 2.5 cm. Aspect: Upright, erect. Texture: Smooth, glabrous. Color: Close to 147A overlain with 187A.

*Foliage description.*—Arrangement: Alternate, simple. Length: About 23 cm. Width: About 13 cm. Shape: Ovate. Apex: Acuminate. Base: Obtuse. Margin: Entire. Texture, upper and lower surfaces: Smooth, glabrous; leathery. Venation pattern: Pinnate. Color: Developing leaves, upper surface: Centers, irregular sectors of close to 147A or close to 194A overlain with close to 187A; towards the margins, close to 155D overlain with close to 187A. Developing leaves, lower surface: Centers, irregular sectors of close to 147B or close to 194C overlain with close to 187A; towards the margins, close to 155D overlain with close to 187A. Fully expanded leaves, upper surface: Centers, irregular sectors of close to 147A or close to 194A faintly overlain with close to 187A; towards the margins, close to 155D faintly overlain with close to 187A. Fully expanded leaves, lower surface: Centers, irregular sectors of close to 147B or close to 194C faintly overlain with close to 187A; towards the margins, close to 155D faintly overlain with close to 187A. Venation, upper and lower surfaces: Close to 187A. Petiole: Length: About 2.5 cm. Diameter: About 5 mm. Texture, upper and lower surfaces: Smooth, glabrous; leathery. Color, upper and lower surfaces: Close to 187A.

Flower description: Flower development has not been observed on plants of the new *Ficus.*

Disease/pest resistance: Plants of the new *Ficus* have not been observed to be resistant to pathogens and pests common to *Ficus.*

Temperature tolerance: Plants of the new *Ficus* have been observed to tolerate temperatures from 14 to 40° C.

It is claimed:

1. A new and distinct *Ficus* plant named 'Belize', as illustrated and described.

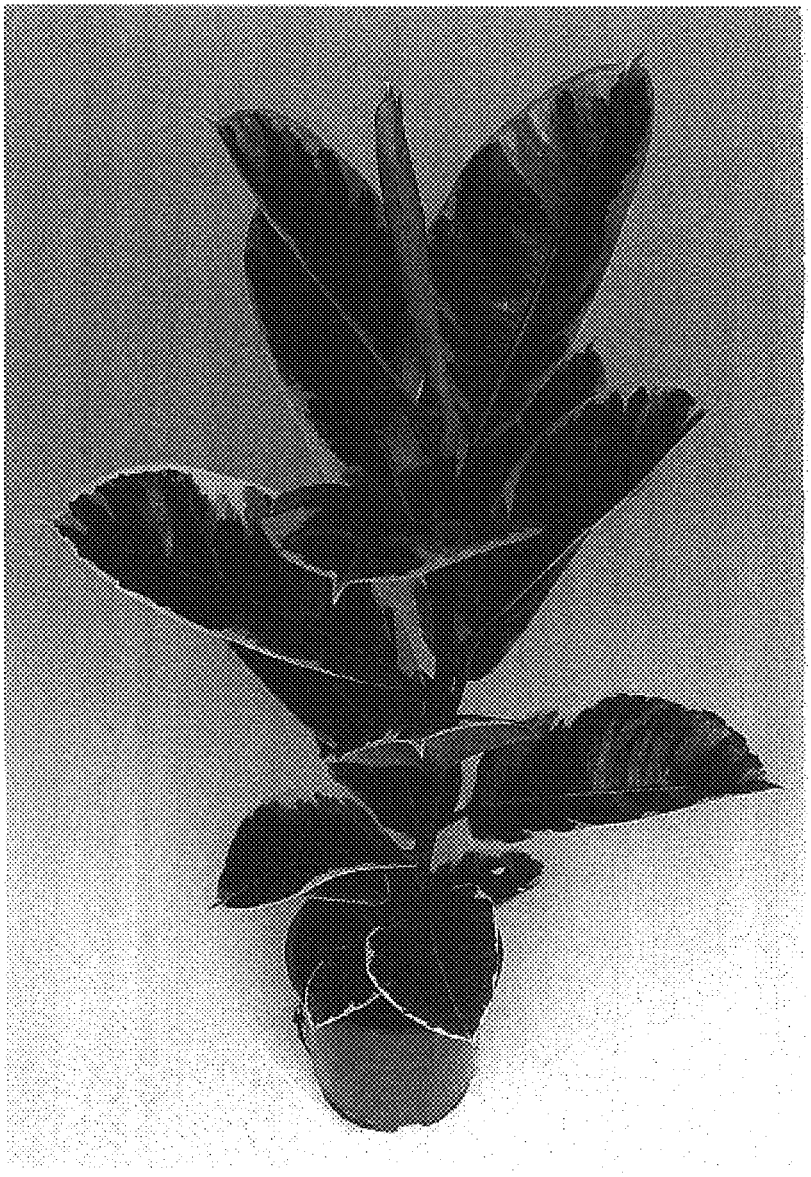

* * * * *